United States Patent [19]

Wheeler

[11] 4,439,184
[45] Mar. 27, 1984

[54] TWO-DOSE SYRINGE

[75] Inventor: Robert P. Wheeler, Keene, N.H.

[73] Assignee: Concord Laboratories, Inc., Keene, N.H.

[21] Appl. No.: 373,867

[22] Filed: May 3, 1982

[51] Int. Cl.³ .............................................. A61M 5/00
[52] U.S. Cl. ..................... 604/90; 604/191
[58] Field of Search ............... 604/89, 90, 82, 191, 604/187, 238; 222/386, 129, 135–137

[56] References Cited

U.S. PATENT DOCUMENTS

| | | | |
|---|---|---|---|
| 2,591,046 | 4/1952 | Brown | 604/90 |
| 3,881,484 | 5/1975 | Gidcumb, Jr. | 604/89 |
| 3,985,122 | 10/1976 | Topham | 604/191 |
| 4,067,333 | 1/1978 | Reinhardt et al. | 604/191 |
| 4,188,949 | 2/1980 | Antoshkiw | 604/191 |
| 4,235,235 | 11/1980 | Bekkering | 604/238 |

Primary Examiner—John D. Yasko
Attorney, Agent, or Firm—Sewall P. Bronstein; George W. Neuner

[57] ABSTRACT

A syringe for delivering two separated bodies of fluid comprising: a first piston for separating the two bodies of fluid; a second piston for pushing the two bodies of fluid out of the syringe; and a fluid chamber having a no-pass zone in which the pistons can slide and which has a cross section that each of the pistons substantially fills, preventing the passing of fluid around the pistons when they are in the no-pass zone, an output zone to direct fluid pushed out of the syringe by the pistons, and a bypass zone, for receiving the first piston, which connects the no-pass and output zones and which has a cross section that the first piston is unable to fill, so that when the first piston enters the bypass zone the fluid between the first and second pistons can pass around the first piston to the output zone. In a preferred embodiment the bypass zone has ridges projecting in from its wall, which push portions of the first piston away from that wall, allowing fluid to flow around the first piston; the output portion forms a nozzle designed to fit into, and make a seal with, a urethra; and the two bodies of fluid are a lubricating antiseptic and a lubricating anesthetic for use in preparing a patient for catheterization.

18 Claims, 8 Drawing Figures

TWO-DOSE SYRINGE

BACKGROUND OF THE INVENTION

This invention relates generally to syringes, and in particular to two-dose syringes, which deliver two separated bodies of fluid, such as a lubricating antiseptic and a lubricating anesthetic for preparing the urethra for catheterization.

It is often desirous to inject two different liquids which have previously been kept separated into one place. For example, in preparing a urethra for the insertion of a catheter, it is often desirous to inject into the urethra both a lubricating antiseptic, such as iodophore jelly, and a lubricating anesthetic, such as lidocaine hydrochloride jelly. The antiseptic decreases the chance of infection, and the anesthetic the pain, associated with the insertion of the catheter. The lubricating properties of both the antiseptic and the anesthetic make it easier for the catheter to be slid into the urethra.

Various two-dose syringes have been previously known. One common variety of such syringes is shown in U.S. patents numbered U.S. Pat. Nos. 2,687,728, 2,939,459, and 4,044,758, issued to Copen, Lazarte et al. and Patel, respectively. This type of two-dose syringe has a cylindrical chamber with a plunger at one end, a needle at the other that sticks into the chamber, and a piston in between the plunger and the needle which separates two bodies of fluid and which is punctured when the plunger pushes it into the needle. A problem with this type of two-dose syringe is that it is relatively expensive to make, since its requirement that a needle be inserted in the chamber means that it can not be made by a simple molding process. Another category of two-dose syringes is shown by U.S. patents numbered U.S. Pat. Nos. 3,091,240 and 3,667,652, issued to McConnaughey et al. and Morane et al., respectively. The syringes both have a barrier between their respective two bodies of fluid, which barriers either collapse or open at a previously made perforation when pressure is generated by the syringe's plunger. One of the problems with these syringes is that their fluid separating barriers are less secure than those used in other two-dose syringes. The two-dose syringes shown in U.S. patents numbered U.S. Pat. Nos. 3,680,558 and 4,188,949 issued to Kapelowitz and Antoshkiw, respectively, both require two plungers, one within the other to operate. The Antoshkiw syringe, in addition to its complexity, does not have means for preventing communication between the two liquids it holds. The Kapelowitz syringe, on the other hand, requires a valve to function.

None of the prior art discussed above discloses a two-dose syringe which is particularly well suited for injecting two preloaded, separate fluids into the urethra in preparation for the insertion of a catheter.

Accordingly, an object of the present invention is to provide a two-dose syringe which avoids the above stated problems in the prior art. It is a further object to provide a two-dose syringe which is simple and inexpensive to make. It is yet another object to provide a two-dose syringe which is quick and easy to use. And it is yet a further object to provide a two-dose syringe which is suited for injecting fluids into the urethra, such as in preparation for catheterization.

Other objects and advantages of the present invention will be apparent from a reading of the present specification, or from the practice of the invention herein disclosed.

SUMMARY OF THE INVENTION

Briefly, the above advantages are obtained in accordance with the present invention by providing a syringe for delivering two separated bodies of fluid which has a first piston for separating the two bodies of fluid, a second piston for pushing the two bodies of fluid out of the syringe, and a fluid chamber. The fluid chamber has a no-pass zone in which the pistons can slide and which has a cross section that each of said pistons substantially fills, preventing the passing of fluid around the pistons when they are in the no-pass zone. The fluid chamber also has an output zone, to direct fluid pushed out of the syringe by said pistons, and a bypass zone, connecting the no-pass and output zones. The bypass zone of the fluid chamber is capable of receiving the first piston, and it has a cross section that the first piston is unable to fill, so that when the first piston enters the bypass zone the fluid between the first and second pistons can pass around the first piston to the output zone. In a preferred embodiment, the first piston is made of a compressible, resilient material, such as rubber, and the bypass zone has one or more ridges which project into the fluid chamber from its wall to push a portion of the first piston away from that wall, so that fluid can flow around the first piston when it enters the bypass zone. In a preferred embodiment, the output zone of the fluid chamber is shaped into a nozzle with a tip which has the external shape and diameter to fit into a urethra, and the syringe contains two bodies of fluid for preparing a urethra for catheterization, one a lubricating antiseptic and the other a lubricating anesthetic.

In an alternative embodiment, which is designed to cause the two separated fluids contained in the syringe to mix before they are injected by the syringe, the bypass zone is shaped so that the first piston can be pushed through the bypass zone by the second piston and the output zone contains a no-pass portion in which the first piston can slide and which has a cross section that the first piston substantially fills, preventing the passing of fluid around the first piston when it is in the no-pass portion.

THE DRAWINGS

The following detailed description is to be read in conjunction with the accompanying drawings, in which FIG. 1 is a planar side view of the preferred two-dose syringe of the present invention;

DETAILED DESCRIPTION OF THE PREFERRED EMBODIMENT

Figure 1:
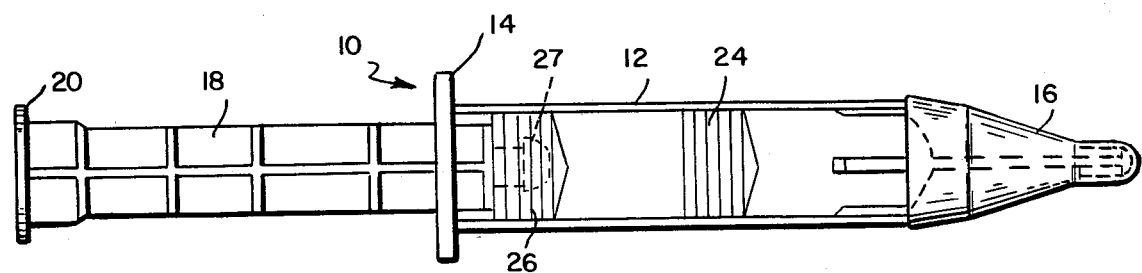

Referring to FIG. 1 of the drawings, a preferred embodiment 10 of the present invention is shown which is a preloaded two-dose syringe for use in preparing a human urethra for the insertion of a catheter. Syringe 10 has a cylindrical body, or tube, 12, which is preferably made of an inexpensive substantially transparent plastic material that can be easily molded, such as polypropylene. Tube 12 terminates at one end with finger piece 14, which makes it easier for the tube to be held when being used. On the other end of tube 12 is a detachable cap 16, preferably made of a polyolefin such as polyethylene. Cap 16 makes a fluid-tight compression fit with the end of syringe 10 over which it is placed. This prevents fluid from escaping, and it keeps the end of the syringe covered by cap 16 clean before the syringe is used. Syringe 10 has a plunger 18 for pushing fluid out of the syringe. On the end of plunger 18 is a thumb piece 20 against which a thumb can be pressed to move the plunger. In the preferred embodiment, syringe 10 extends slightly more than three and one half inches from finger piece 14 to the tip of cap 16.

Figure 2:
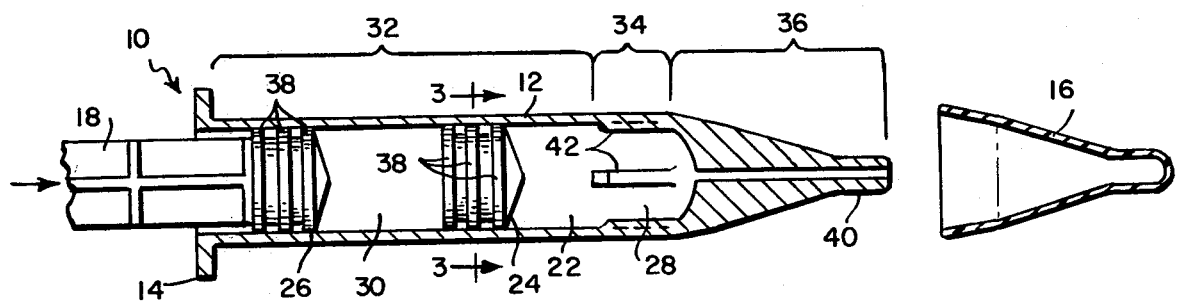
FIG. 2 is a longitudinal section of the syringe of FIG. 1, before use, with its cap removed.

Referring to FIG. 2, a longitudinal cross section of syringe 10, with cap 16 removed, is shown. Cylindrical tube 12 is hollow, and it defines a fluid chamber 22 in which are placed two pistons, a first piston 24 and a second piston 26. Pistons 24 and 26 are preferably made of a compressible, resilient material such as butyl rubber, and they are substantially similar in shape, except that second piston 26 has an opening in its back for receiving, and making a locking fit with, protrusion 27 of plunger 18. Plunger 18 forms an extension of second piston 26 which aids in pushing piston 26 because it extends out of chamber 22. First piston 24 divides two separated bodies of fluid which are located in chamber 22, a first body of fluid 28 located between cap 16 and first piston 24 and a second body of fluid 30 located between first piston 24 and second piston 26. In the preferred embodiment used for preparing a urethra for catheterization, first fluid 28 is comprised of 5 ml. of iodophor jelly, a lubricating antiseptic, and second fluid 30 is comprised of 5 ml. of lidocaine hydrochloride jelly, a lubricating anesthetic. In a preferred embodiment, however, the order in which the two fluids are loaded can be changed with little effect. In other embodiments of the invention, particularly those in which a two-dose syringe is used for purposes other than preparing a urethra for catheterization, the first and second fluids can be comprised of differrent substances.

As indicated in FIG. 2, the length of fluid chamber 22 is divided into three zones, a no-pass zone 32, a bypass zone 34, and an output zone 36.

Figure 3:
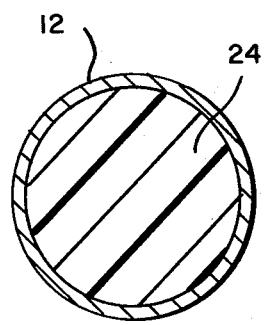
FIG. 3 is a cross section of the syringe of FIG. 2 taken along the line 3—3.

No-pass zone 32 is shaped so that both piston 24 an 26 can slide within it. As indicated in FIG. 3, the cross section of no-pass zone 32 is such that both the first and second pistons substantially fill that cross section, preventing the flow, or passing, of fluid around either piston when they are in that zone of chamber 22. In the preferred embodiment, pistons 24 and 26 each have three circular compressible ribs 38, of a slightly larger diameter than the circular inner wall of no-pass zone 32, for making a slidable, but fluid-tight seal with that inner wall and for firmly holding each of the pistons in alignment with the longitudinal axis of syringe 10.

Output zone 36 of chamber 22 is used to direct the fluid pushed out of syringe 10 by pistons 24 and 26. In the preferred embodiment, output zone 36 includes a narrowing of chamber 22. This narrowing forms a nozzle with a tip 40 that has an external shape and diameter designed to fit into, and make a seal with, a human urethra. Tip 40 is generally cylindrical, approximately three tenths of an inch long, approximately two tenths of an inch wide, and its forward edge is rounded to make its insertion into a urethra more easy. Of course, in other embodiments of the invention, the output zone could contain another sort of tips for injecting the fluids contained in the syringe, such as a hypodermic needle for injecting fluid beneath a patient's skin.

Figure 4:
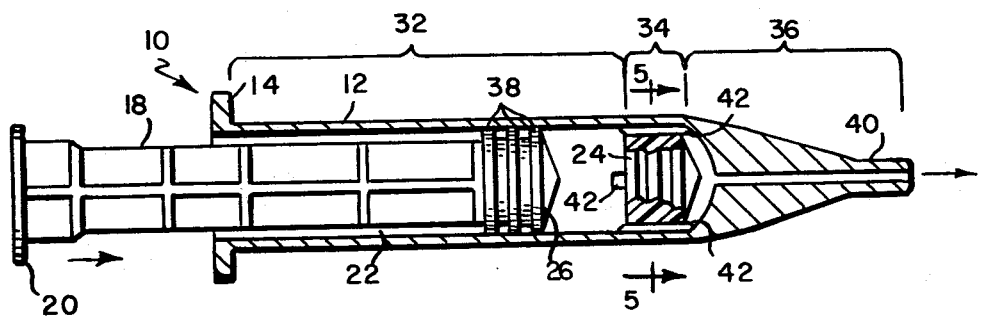
FIG. 4 is a longitudinal section of the syringe of FIG. 1, after partial use, with its cap removed.
Figure 5:
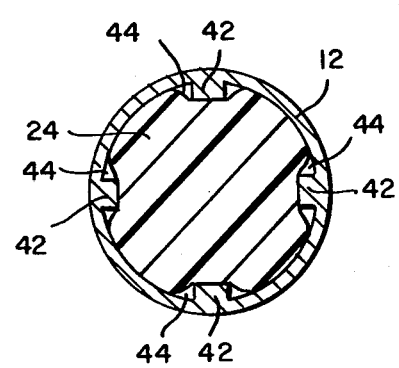
FIG. 5 is a cross section of the syringe of FIG. 4 taken along the line 5—5.

Bypass zone 34 connects no-pass zone 32 and output zone 36. It is designed to receive first piston 24, as shown in FIG. 4, and is provided with means for allowing the fluid between first and second pistons 24 and 26 to pass around, or bypass, the first piston when that piston is located in the bypass zone. As shown in FIG. 5, bypass zone 34 has a cross section that the first piston is unable to fill. Thus when the first piston enters the bypass zone, the fluid between pistons 24 and 26 can flow, or pass, around the first piston to the output zone. In the preferred embodiment, bypass zone 34 includes four ridges 42 which project approximately three one hundredths of an inch into chamber 22, which is approximately six tenths of an inch in diameter, from that chamber's inner wall. As can be seen in FIG. 5, in which the relative size of ridges 42 is exaggerated for purposes of illustration, these ridges prevent the first piston from filling the cross section of the bypass zone. When first piston 24 enters the bypass zone, each of the ridges pushes a portion of the first piston away from the inner wall of chamber 22, making small openings 44 through which fluid can flow around the first piston.

It is desirable that the bypass zone be shorter than the combined axial dimensions of pistons 24 and 26. This prevents both pistons from fitting into the bypass zone, and thus it prevents fluid from being able to flow around second piston 26, which, if it were to happen, would decrease the ability of that piston to push fluid out the proper end of the syringe.

In alternative embodiment of the invention, the bypass zone of syringe 10 might have other cross sections than that shown in FIG. 5. For example, grooves could be placed in the wall of chamber 22 in place of the ridges 42 used in the preferred embodiment. Such grooves would give the bypass zone a cross section that the first piston would be unable to fill, and, thus, fluid could flow around the first piston once it entered such a grooved bypass zone. Similarly the bypass zone could have a cross section too large in diameter for the first piston to fill. In yet another embodiment, the bypass zone could have a cross section divided into separate channels, a first of which received the first piston and at least one of which formed a bypass passage separated from first channel. In such an embodiment the bypass passage, or passages, would each have an opening near the boundary of the no-pass and the bypass zones and another opening near the output zone, so that once the first piston had entered the bypass zone, fluid between the first and second pistons would be free to flow through such a bypass passage, around the first piston, to the output zone.

When syringe 10 is to be used, cap 16 is removed so that it will no longer block the flow of fluid out of the nozzle of the syringe. Until cap 16 is removed, the resistance of fluids 28 and 30 to compression and the air pressure outside the syringe make it difficult to move pistons 24 and 26. Thus, if it is desirable to distribute and store syringe 10 in a shortened form, plunger 18 can be kept separated from second piton 26, without any danger of the piston falling out, until the syringe is ready for use, at which time protrusion 27 of plunger 18 could be inserted into the second piston.

Once cap 16 is removed, fluid can flow out of tip 40, and syringe 10 is ready for use. The cylindrical tube 12 would then normally be held between the index and middle fingers, with the thumb pressed against thumb piece 20. Then tip 40 would be inserted into the urethra. If there is not already a slight amount of the lubricating iodophor jelly on tip 40 when cap 16 is removed, a slight push of plunger 18 can cause a small amount of such jelly to flow out of tip 40, lubricating that tip before its insertion into the urethra.

Once syringe 10 is inserted into the urethra, fluids 28 and 30 can be sequentially injected with one easy push of the thumb upon plunger 18. When the syringe is first inserted, the position of pistons 24 and 26 is basically that shown in FIG. 2, with both pistons in no-pass zone 32 of chamber 22. When plunger 18 is pushed, second piston 26 slides toward tip 40, generting a pressure is second fluid 30 that causes first pison 24 to also move toward tip 40. This in turn pushes first fluid 28 out through tip 40 into the urethra. During the beginning of the stroke of plunger 18, the first piston makes a complete seal with the wall of the no-pass zone of chamber 22, and thus the second fluid cannot pass around the first piston and only the first fluid exits tip 40. But once the movement of plunger 18 reaches a point where first piston 24 has been forced between ridges 42 of bypass zone 34, as shown in FIGS. 4 and 5, the ridges push a portion of the first piston away from the inner wall of chamber 22, and the second fluid is free to bypass the first piston. After this point in the stroke of plunger 18, the second fluid is ejected through tip 40 into the urethra.

Figure 6:
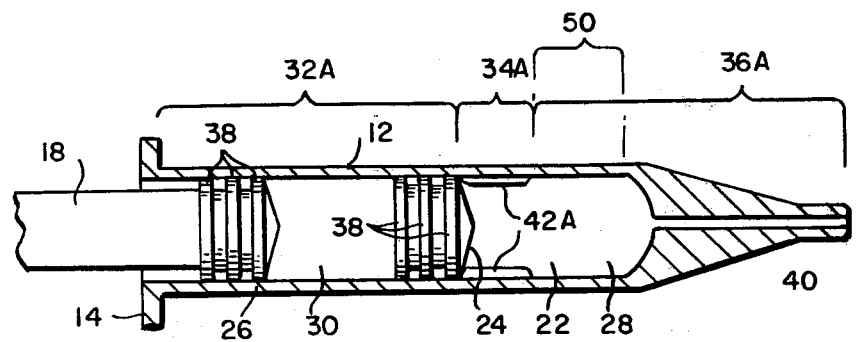
FIG. 6 is a longitudinal section of a syringe according to another embodiment of the invention.
Figure 7:
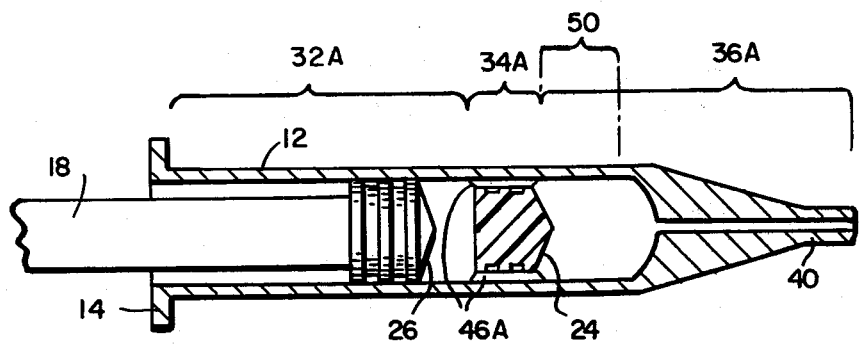
FIG. 7 is a longitudinal section of the syringe of FIG. 6 after partial use.
Figure 8:
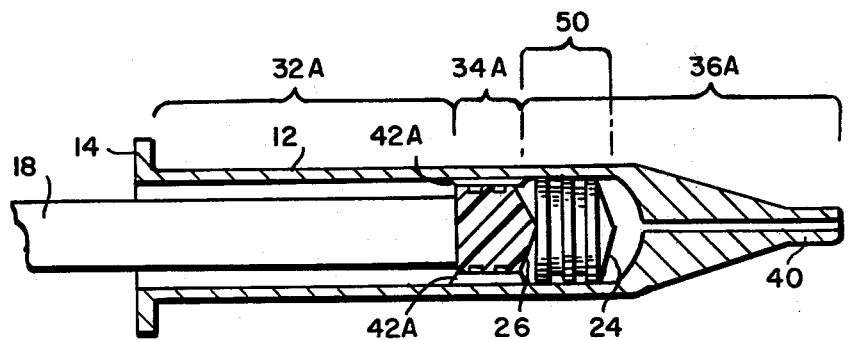
FIG. 8 is a longitudinal section of the syringe of FIGS. 6 and 7 after still further use.

Referring to FIGS. 6, 7, and 8, an alternative embodiment of the invention is shown in which elements corresponding to those of the embodiment shown in the earlier figures are correspondingly numbered. This embodiment is particularly suitable for applications in which it is desired to mix the two separated fluids held by a two-dose syringe just before they are injected. The embodiment shown in FIGS. 6-8 is distinguished from that shown previously by the fact that its bypass zone 34A is located very near the initial position of the first piston 24 and its output zone 36A contains a no-pass portion 50 of tube 12 which as a cross section similar to that of no-pass zone 32A.

In operation the syringe o FIGS. 6-8 works as follows: when plunger 18 is moved toward the output zone 36A the pressure generated by second piston 26 pushes first piston 24 into bypass zone 34A and between ridges 42A of that zone, as shown in FIG. 7. Once first piston 24 is in bypass zone 34A, the fluid between pistons 24 and 26 is free to pass around piston 24 into output zone 36A, where it mixes with the fluid between piston 24 and tip 40 and is pushed out of the syringe. When plunger 18 is pushed in further, second piston 26 comes in contact with first piston 24, enters bypass zone 34A, and finally pushes the first piston out of the bypass zone into the no-pass portion 50 of output zone 36A, as is shown in FIG. 8. Once the first piston enters the no-pass portion 50 of the output zone, it fills the cross section of that no-pass portion so that the piston's sides once again make a substantially fluid-tight seal with the wall of tube 12, preventing fluid from passing around that piston. Further inward motion of plunger 18 causes the second piston to push the first piston along the no-pass portion of the output zone, forcing the mixed fluid between the first piston and tip 40 out of the syringe. Since the length of bypass zone 34A is too short to allow fluid to bypass both the first and second pistons at the samd time, no significant quantity of fluid is allowed to escape around the second plunger.

In the syringe of FIGS. 6-8 the ridges 42A could be helical in shape to provide turbulence to the fluid which bypasses the first piston and thus better mix it with the fluid located in front of the first piston. It should also be seen that the ridged bypass zone 34A shown in FIGS. 6-8 could be replaced with a different type of bypass zone, such as one having bypass grooves in the wall of tube 12.

It can be seen that the invention provides a means for injecting two separated bodies of fluid which is relatively simple and inexpensive, which is easy and quick to use, and which is particularly suited to preparing the urethra for the insertion of a catheter.

It is not intended that the invention be limited to or by the aforesaid description and accompanying drawings of only two embodiments thereof, but only to the subject matter claimed hereinafter and its equivalents.

What is claimed is:

1. A syringe for delivering two separated bodies of fluid, said syringe comprising:
   a first piston made of a compressible, resilient material for separating said two bodies of fluid;
   a second piston for pushing said two bodies of fluid out of said syringe; and
   a walled fluid chamber having a no-pass zone in which said pistons can slide and which has a cross section shaped so that each of said pistons can conform to its wall, preventing the passing of fluid around said pistons when they are in said no-pass zone; an output zone to direct fluid pushed out of said syringe by said pistons; and a bypass zone, for receiving said first piston, which connects said no-pass and output zones and which has at least one ridge projecting into said fluid chamber from its wall to push a portion of said first piston away from said wall when said first piston enters said bypass zone so that the fluid between said first and second pistons can pass around said first piston to said output zone.

2. A syringe according to claim 1 wherein said first piston is made of rubber.

3. A syringe according to claim 1 wherein said walled chamber is cylindrical in both said no-pass zone and said bypass zone.

4. A syringe for delivering two separated bodies of fluid into the urethra, said syringe comprising:
   a first piston made of a compressible, resilient material for separating said two bodies of fluid;
   a second piston for pushing said two bodies of fluid out of said syringe; and
   a walled fluid chamber having a no-pass zone in which said pistons can slide and which has a cross section shaped so that each of said pistons conforms to its wall, preventing the passing of fluid around said pistons when they are in said no-pass zone; a nozzle to direct fluid pushed out of said syringe by said pistons, which nozzle has a tip with an external shape and size to fit into a urethra; and a bypass zone, for receiving said first piston, which connects said no-pass and output zones and which has at least one ridge projecting into said fluid chamber from its wall to push a portion of said first piston away from said wall when said first piston enters said bypass zone so that the fluid between said first and second pistons can pass around said first piston to said output zone.

5. A syringe for delivering two separated bodies of fluid into the urethra, said syringe comprising:
a first piston for separating said two bodies of fluid;
a second piston for pushing said two bodies of fluid out of said syringe;
a fluid chamber having a no-pass zone in which said pistons can slide and which has a cross section that each of said pistons substantially fills, preventing the flow of fluid around said pistons when they are in said no-pass zone; a nozzle to direct fluid pushed out of said syringe by said pistons, which nozzle has a tip with an external shape and size to fit into, and make a seal with, a urethra; and a bypass zone, for receiving said first piston, which connects said no-pass zone and said nozzle and which has a cross section that said first piston is unable to fill, so that, when said first piston enters said bypass zone, the fluid between said first and second pistons can pass around said first piston to said nozzle;
a removable nozzle blocking means for preventing fluid from exiting said nozzle until said blocking means is removed;
a first body of fluid between said blocking means and said first piston;
a second body of fluid between said first and second pistons;
wherein said first piston is made of a compressible, resilient material, said fluid chamber has a wall and said bypass zone has at least one ridge projecting into said fluid chamber from its wall to push a portion of said first piston away from said wall when said first piston enters said bypass zone so that the fluid between said first and second pistons can pass around said first piston to said nozzle; and
wherein one of said bodies of fluid is an antiseptic lubricant and the other is an anesthetic lubricant.

6. A syringe according to claim 5 further wherein said nozzle blocking means includes a removable cap which fits over the tip of said nozzle and keeps it clean.

7. A syringe according to claim 5 in which said antiseptic lubricant includes iodophor jelly and said anesthetic lubricant includes lidocaine hydrochloride jelly.

8. A two dose syringe comprising:
an integral fluid chamber having an open end, a partially closed end, and a bypass zone located axially between said open end and said partially closed end, said bypass zone containing one or more ridges on the inside wall of said fluid chamber reducing the cross-sectional area of said chamber in the bypass zone;
a first piston made of a compressible, resilient material, disposed in said fluid chamber to create a sliding, fluid-tight seal with the inner wall of said chamber, thus sealing the open end of the chamber; and
a second piston located axially between said bypass zone and said first piston to divide said chamber into two sections, and not structurally connected with said first piston, said second piston being formed of a compressible, resilient material and forming a sliding, fluid-tight seal with the inner wall of said chamber.

9. A syringe in accord with claim 8 wherein said partially closed end includes a narrowing of said chamber to form a nozzle.

10. A syringe in accord with claim 8 wherein said first piston is attached to a plunger to facilitate the dispensing of fluids from said syringe.

11. A syringe in accord with claim 8 wherein said bypass zone is shorter axially than the combined axial dimensions of said first and second pistons.

12. A syringe in accord with claim 8 wherein said bypass zone is located adjacent to said partially open end.

13. A syringe in accord with claim 8 wherein said bypass zone is located in the midsection region of said chamber.

14. A pre-filled two dose syringe comprising:
an integral fluid chamber having an open end, a partially closed end, and a bypass zone located axially between said open end and said partially closed end, said bypass zone containing one or more ridges of the inside wall of said fluid chamber reducing the cross-sectional area of said chamber in the bypass zone;
a first piston made of a compressible, resilient material, disposed in said fluid chamber to create a sliding, fluid-tight seal with the inner wall of said chamber, thus sealing the open end of the chamber; and
a second piston located axially between said bypass zone and said first piston to divide said chamber into two sections, and not structurally connected with said first piston, said second piston being formed of a compressible, resilient material and forming a sliding, fluid-tight seal with the inner wall of said chamber;
a removable cap sealably covering said partially open end to prevent leakage;
a first fluid substance located between said cap and said second piston; and
a second fluid substance located between said first and second pistons.

15. A syringe in accord with claim 14 wherein one of said fluid substances is an antiseptic lubricant and the other of said fluid substances is an anesthetic lubricant.

16. A syringe in accord with claim 14 wherein said bypass zone is located adjacent to said partially closed end, said first fluid substance is an antiseptic lubricant, and said second substance is an anesthetic lubricant.

17. A syringe in accord with claim 14 wherein said first fluid substance and said second fluid substance are the same substance.

18. A method for preparing a urethra for catheterization comprising injecting an antiseptic lubricant and an anesthetic lubricant into said urethra using a prefilled syringe;
said prefilled syringe comprising an integral fluid chamber having an open end, a partially closed end, and a bypass zone located axially between said open end and said partially closed end, said bypass zone containing one or more ridges on the inside wall of said fluid chamber reducing the cross-sectional area of said chamber in the bypass zone;
a first piston made of a compressible, resilient material, disposed in said fluid chamber to create a sliding, fluid-tight seal with the inner wall of said chamber, thus sealing the open end of the chamber; and a second piston located axially between said bypass zone and said first piston to divide said chamber into two sections, and not structurally connected with said first piston, said second piston being formed of a compressible, resilient material and forming a sliding, fluid-tight seal with the inner wall of said chamber; a removable cap sealably covering said partially open end to prevent leakage; a first fluid substance located between said cap and said second piston and; a second fluid substance located between said first and second pistons;

wherein said first piston is moved forward part way in said syringe by pressing a plunger, thereby dispensing said first fluid substance into said urethra and moving said second piston into the bypass zone; and wherein said first piston is further moved completely forward in said syringe by pressing said plunger as far as it will go, thereby dispensing said second fluid substance into the urethra.

* * * * *